United States Patent [19]

Harandi et al.

[11] Patent Number: 5,166,454

[45] Date of Patent: * Nov. 24, 1992

[54] ETHERIFICATION PROCESS WITH HYDROGEN REJUVENATION

[75] Inventors: Mohsen N. Harandi, Lawrenceville; Hartley Owen, Belle Mead, both of N.J.

[73] Assignee: Mobil Oil Corporation, Fairfax, Va.

[*] Notice: The portion of the term of this patent subsequent to May 14, 2008 has been disclaimed.

[21] Appl. No.: 695,844

[22] Filed: May 6, 1991

Related U.S. Application Data

[63] Continuation-in-part of Ser. No. 495,667, Mar. 19, 1990, Pat. No. 5,015,782.

[51] Int. Cl.$^5$ ............................................. C07C 41/06
[52] U.S. Cl. .............................. 568/697; 203/DIG. 6
[58] Field of Search ................. 568/697; 203/DIG. 6

[56] References Cited

U.S. PATENT DOCUMENTS

| | | | |
|---|---|---|---|
| 4,417,088 | 11/1983 | Miller | 585/533 |
| 4,906,788 | 3/1990 | Scott et al. | 568/697 |
| 5,013,329 | 5/1991 | Bell et al. | 568/697 |
| 5,015,782 | 5/1991 | Harandi et al. | 568/697 |

OTHER PUBLICATIONS

Chu et al., Ind. Eng. Chem. Res. 1987, 26, 365-369.

*Primary Examiner*—Howard T. Mars
*Attorney, Agent, or Firm*—Alexander J. McKillop; Charles J. Speciale; L. G. Wise

[57] ABSTRACT

A multistage process for etherifying $C_4+$ aliphatic hydrocarbon feedstock containing isoalkane including the step of contacting the hydrocarbon feedstock with dehydrogenation catalyst at elevated temperature under dehydrogenation reaction conditions to obtain $C_4+$ isoalkene and hydrogen, and separating dehydrogenation effluent to obtain an olefinic stream rich in isoalkene and a hydrogen stream.

The olefinic stream and aliphatic alcohol are contacted in an esterification stage under partial etherification conditions with a regenerable inorganic metal oxide acid solid catalyst to convert a major amount of the isoalkene to $C_5+$ tertiary-alkyl ether. In the preferred embodiment, effluent recovered from the first stage containing ether product, unreacted alcohol and unreacted olefin including isoalkene is charged to a second stage catalytic distillation column containing solid acid resin etherification catalyst in a plurality of fixed bed catalysis-distillation zones to complete substantially full etherification of isoalkene.

At least a portion of recovered hydrogen is employed for contacting the regenerable etherification catalyst to remove feedstock impurity and coke and to restore acid activity. In the manufacture of MTBE, the alcohol consists essentially of methanol and the $C_4+$ feedstock consists predominantly of $C_4$ hydrocarbons containing isobutane. The first etherification stage catalyst may comprise medium pore zeolite and the second stage catalyst may comprise polymeric sulfonic acid resin.

16 Claims, 1 Drawing Sheet

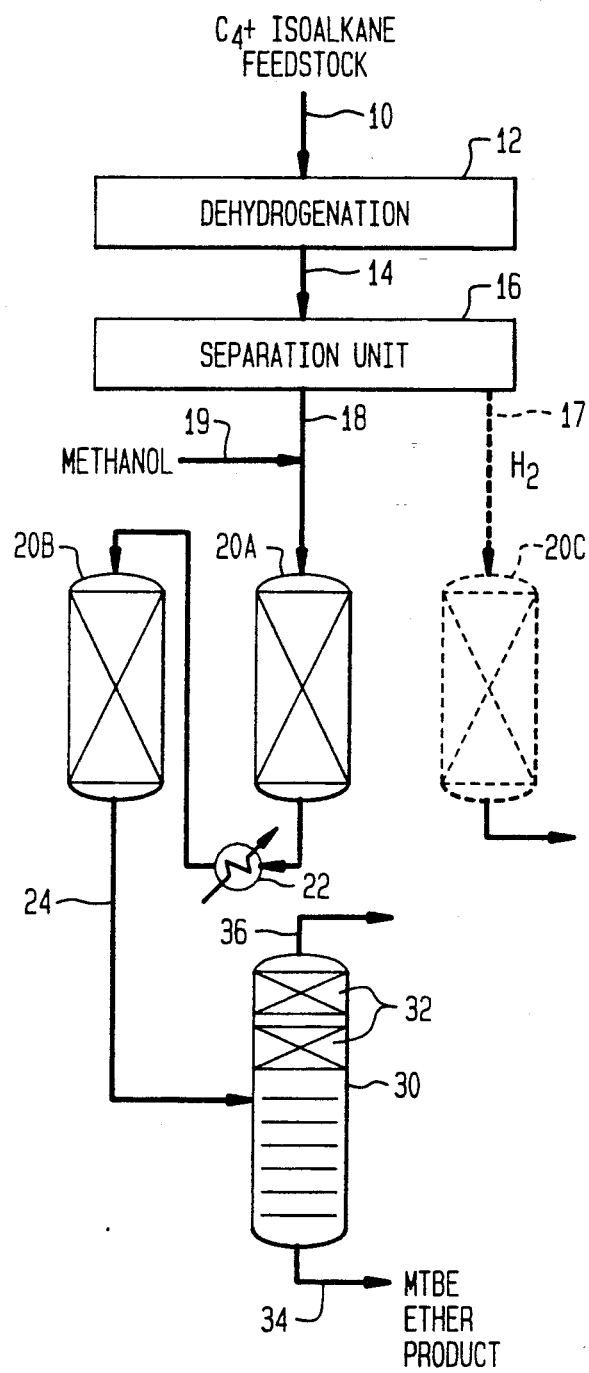

ETHERIFICATION PROCESS WITH HYDROGEN REJUVENATION

REFERENCE TO COPENDING APPLICATION

This application is a continuation-in-part of U.S. patent application Ser. No. 07/495,667, filed Mar. 19, 1990, now U.S. Pat. No. 5,015,782 incorporated herein by reference.

FIELD OF THE INVENTION

The present invention relates to a multi-stage process for preparing ethers in high yield and purity. More particularly it relates to a technique for rejuvenating catalyst used in preparing ethers, such as methyl t-butyl ether (MTBE) and t-amyl methyl ether (TAME).

BACKGROUND OF THE INVENTION

Recent efforts have been made in the field of gasoline blending to increase gasoline octane performance without the addition of deleterious components such as tetraethyl lead and benzene. It has been found that lower molecular weight unsymmetrical ethers such as MTBE and TAME can be added to $C_5$-$C_{10}$ hydrocarbon-containing gasoline products in order to increase octane number. The research octane number (RON) of MTBE has been listed at 115 (Lander, E.P. et al, "National Petroleum Refiners Association Annual Meeting", San Francisco, Calif., March 20–24, 1983). The blending octane number of MTBE has been calculated over various concentrations and some of the readings are: RON, 115-135; MON (motor octane number), 98-110; and (RON & MON)/2, 106-122.5 (Pecci, G. et al, *Hydrocarbon Processing*, 1977, 56, 98). Blending octane number rises when MTBE concentration is decreased and saturates concentration of the base fuel is increased.

Conventional etherification processing uses as catalyst a macroreticular cation exchange resin in the hydrogen form. An example of such a catalyst is "Amberlyst 15". A resin catalyst gives a high conversion rate but is unstable at elevated temperatures (above about 90° C.). When overheated, the resin catalyst releases sulfonic and sulfuric acids. In addition leaching of acid substances from the resin catalyst even at normal operating temperatures causes a reverse reaction—decomposition of ether products to starting materials—to occur upon distillation of ether product. Overall yield is thereby significantly decreased (see U.S. Pat. No. 4,182,913 to Takesono et al).

Etherification reactions conducted over a resin catalyst such as "Amberlyst 15" are usually conducted in the liquid phase below a temperature of about 90° C. and at a pressure of about 200 psig. Equilibrium is more favorable at lower temperatures but the reaction rate decreases significantly. Also excess methanol appears to be required to achieve acceptable selectivity over "Amberlyst 15" (see Chu et al, *Industrial Engineering and Chemical Research*, Vol. 26, No. 2, 1987, 365-369).

Some recent efforts in the field of etherification reactions have focused on the use of acid medium-pore zeolite catalyst for highly selective conversion of iso-olefin and alcohol starting materials. Examples of such zeolite catalysts are ZSM-4, ZSM-5, ZSM-11, ZSM-12, ZSM-23, ZSM-35, ZSM-50 and zeolite Beta. Due to lower acidity as compared to resin catalysts, the zeolites need to be employed at higher reaction temperature to achieve the desired conversion rates. These solid acid catalyst particles are much more thermally stable than resin catalyst, are less sensitive to methanol-to-isobutene ratio, give no acid effluent, and are easily and quickly regenerated (see Chu et al, "Preparation of Methyl tert-Butyl Ether (MTBE) over Zeolite Catalysts", *Industrial Engineering and Chemical Research*, op cit.).

It is an object of the present invention to provide a process and apparatus for continuous operation in preparation of t-alkyl ethers from an alcohol and an iso-olefin with a conventional acid resin catalyst whereby the resin catalyst is protected from impurities such as nitrogen compounds, metals, and coke precursors. It is another object of this invention to provide an etherification process with reactivation of thermally-stable catalyst, such as zeolite, employing a non-oxidative gaseous stream.

SUMMARY OF THE INVENTION

An improved process has been found for producing ether by catalytic contact of etherification feedstock comprising alkene, alkanol, ether precursors or mixtures thereof in the presence of at least one deactivating impurity, with thermally stable solid material having acid catalytic activity under etherification conditions. The improvement comprises periodically rejuvenating the solid material by contact with a high temperature stream of hydrogen-containing gas, or other non-oxidative gas, to remove the deactivating impurity.

In one of its aspects, the present invention comprises a multistage process for etherifying a $C_4+$ aliphatic hydrocarbon feedstock containing isobutane, comprising the steps of contacting the hydrocarbon feedstock with dehydrogenation catalyst at elevated temperature under dehydrogenation reaction conditions to produce isobutene and hydrogen; separating dehydrogenation effluent to obtain an aliphatic stream rich in isobutene and a hydrogen stream, at least a portion of which may be employed by catalyst rejuvenation; contacting the aliphatic stream and alkanol under etherification conditions with a regenerable inorganic metal oxide acid solid catalyst to convert isobutene to $C_5+$ tertiary-butyl ether; contacting the etherification catalyst with the hydrogen stream at elevated temperature to rejuvenate the catalyst and restore acid activity; and continuing ether production with rejuvenated catalyst.

This process may be used advantageously to protect sensitive resin catalyst downstream by charging first etherification stage effluent to a second stage, such as a catalytic distillation column containing solid acid resin etherification catalyst in a plurality of fixed bed catalysis-distillation zones to complete substantially full etherification of isoalkene, and recovering $C_5+$ ether as a liquid from the catalytic distillation column.

These and other advantages and features of the invention will be seen in the following description.

DRAWING

The single FIGURE is a schematic diagram of a preferred embodiment of the present process, showing major operating units and flow of reactants and chemical products.

DETAILED DESCRIPTION OF THE INVENTION

In a preferred embodiment, the present inventive process relates to the preparation of MTBE wherein selectivity and yield are increased and destruction of resin catalyst is greatly decreased. Two reaction zones are maintained in series arrangement. A first reaction zone contains solid crystalline acid medium-pore metallosilicate catalyst particles. A second reaction zone contains acid resin catalyst. Mixed feedstock containing methanol and isobutene-containing C4 hydrocarbons is contacted with solid catalyst particles in the first reaction zone under etherification conditions to obtain an intermediate product comprising MTBE and unreacted feedstock. The intermediate product is then withdrawn from the first reaction zone and added to the second zone for contact with acid resin catalyst under etherification conditions. A product containing a major amount of MTBE is then withdrawn from the second reaction zone. The product is fractionated to obtain a purified MTBE which is recovered.

In this description, metric units and parts by weight are employed unless otherwise stated.

The preferred process comprises removing the first etherification reaction zone from on-line contact with the feedstock, regenerating the solid catalyst particles in the first reaction zone, and resuming addition of feedstock to the first reaction zone. The preferred solid acid catalyst particles are aluminosilicate zeolites selected from ZSM-5, ZSM-11, ZSM-12, ZSM-35, ZSM-50, MCM-22 and zeolite Beta. Since the mixed olefinic feedstock contains many impurities, even after treatment in a desulfurization unit and a water wash, the solid acid zeolite catalyst can become highly contaminated after a period of on-line contact with feedstock. Some of the impurities which are absorbed on the zeolite particles are: amines or other nitrogen compounds; oxyenates, such as acetone; metals, such as Al, Fe, Na and Mg; and monomers and oligomers of olefins and diolefins, such as isoprene, butadiene and cyclopentadiene. Diolefinic compounds and other related hydrocarbons are deposited as coke on the surface and interstices of the zeolite and/or resin catalytic particles. It is therefore an objective of the present process to remove feedstock impurities in the first reaction zone concurrently with the preparation of ethers.

The first reaction zone preferably comprises a plurality of catalytic fixed bed reactors operatively connected for swing from production mode to regeneration mode in alternating sequence. A continuous operation is thus maintained when a fixed bed must be removed from service for catalyst to be regenerated. In one embodiment of the process, the first reaction zone comprises at least three catalytic fixed bed reactors whereby two reactors remain operative at all times. Thus iso-olefin-containing feedstock and alcohol contact acid medium-pore zeolite catalyst in a sequential fashion in the first reaction zone.

In an alternative embodiment, the first reaction zone contains reactors other than fixed bed, such as moving bed, slurry, fluidized bed, or ebullated bed. It is within the scope of the present process and apparatus to adjust the number and types of reactors which contain acid zeolite catalyst in order to optimize both product yield and overall energy consumption as would be practiced by one skilled in the art.

Catalyst rejuvenation or regeneration can be achieved by contacting contaminated zeolite catalyst particles with hydrogen or hydrogen-containing gas in a regeneration zone under conditions of temperature and pressure sufficient to remove at least a major amount of impurities from the catalyst particles. Typical rejuvenation conditions include temperature from about 350° C. up to about 540° C. (700°–1000° F.), preferable bout 370°–450° C., and pressure in the range of 100 kPa to 1500 kPa (0–200 psig), although conditions outside these ranges may be employed in some circumstances. Zeolite catalyst particles can be regenerated effectively by stripping with a hot stream of hydrogen gas recovered from dehydrogenation effluent. Hydrogen stripping below 540° C. avoids the problem of inactivating the catalyst by "steaming" which can occur under oxidative regeneration conditions due to water formation. Furthermore, reactivation pressure for hot hydrogen stripping can be much lower than usually employed in oxidative regeneration. It is advantageous during hot hydrogen stripping to decrease the normal operating pressure during interruption of the etherification reaction. This permits use of ordinary carbon steel in construction of the reaction vessels. The present invention also avoids hot spots in the catalyst bed during oxidative regeneration, due to localized exothermic oxidation reactions.

Since zeolite catalyst particles are readily regenerated, the mixed olefinic feedstock can contain a significant amount of impurities. If desired, the step of washing the feedstream with water can be eliminated. Isobutene-containing feedstreams of low quality can be employed in resin-catalyzed etherification reactions if said feedstreams are first contacted with zeolite catalytic particles such as ZSM-5 under conditions of the present process.

The second reaction zone contains an acid resin catalyst which is preferably a macroreticular polystyrene sulfonic acid resin catalyst. In a preferred embodiment the second reaction zone contains a catalytic distillation column containing polystyrenesulfonic acid resin catalyst in a plurality of fixed bed catalysis-distillation units located in the upper half of the distillation column. The reaction section column is preferably operated at a temperature about 10° to 30° C. lower than the temperature of the first reaction zone.

In an alternate embodiment, the second reaction zone is not a catalytic distillation column, but rather a single reactor or plurality of reactors. Reactor configuration can take many forms, for example, fixed bed, stirred slurry (see U.S. Pat. No. 3,940,450 to Lee, incorporated herein by reference), swing or ebullated bed. It is within the scope of the present process to employ for the second reaction zone any reactor configuration for sequencing acceptable to the skilled engineer. The present invention contemplates that an acid resin catalyst be employed following a regenerable etherification catalyst, preferrably in the second reaction zone. In a preferred embodiment, the resin catalyst is "Amberlyst 15".

The present process is an improvement in the conventional process for producing an ether by reacting an olefinic feedstock with an alcohol. The conventional reaction is conducted in the presence of a solid etherification catalyst of the sulfonic resin type in acid form and the olefinic feedstock contains impurities which substantially reduce the activity of the resin catalyst.

The improvement of the present process comprises adding a preliminary step of contacting the olefin and alcohol reactants in the liquid phase with oxidatively regenerable solid acid catalyst particles in a preliminary reaction zone under partial etherification conditions to produce an intermediate stream comprising tert-alkyl ether and unreacted olefin and alcohol, said intermediate stream being substantially free from impurities which reduce catalyst activity. In a preferred embodiment the olefinic feedstock comprises isobutene in an amount of at least about 10 wt. %. Preferably the acid catalyst is aluminosilicate having the structure of ZSM-5 or zeolite Beta and is contained in a swing reactor or slurry type reactor for ease of removal from contact with reactants. Once removed from on-line activity, the acid catalyst is easily rejuvenated at elevated temperature.

Although the preferred alcohol is methanol, suitable substitutes include ethanol or isopropanol (isopropyl alcohol). Of course, use of these substitutes will yield different ether products. It is within the scope of the present process to employ a mixture of lower molecular weight alcohols. Although isobutene is the preferred hydrocarbon feed, other iso-olefin such as 3-methyl-2-butene can be etherified in the present process.

An apparatus for catalytically preparing ethers from olefins and alcohols is presently disclosed. The apparatus comprises a first reaction zone comprising an inlet means for receiving a mixed feedstock comprising olefins and alcohols, a reactor system containing solid acid medium-pore zeolite catalyst particles, and an outlet means for withdrawing intermediate product stream comprising ethers and unreacted feedstock. This apparatus further comprises a secondary reaction zone comprising an inlet means for receiving withdrawn intermediate product, a catalytic distillation column containing solid acid resin etherification catalyst in a plurality of fixed bed catalysis distillation zones, and an outlet means for withdrawing a final etherification product. Also included in the apparatus is a means for transferring intermediate product from the first reaction zone to the second reaction zone.

Referring to the FIGURE, a pre-washed $C_4^+$ aliphatic hydrocarbon feedstock stream 10 containing isobutane is fed to a dehydrogenation reactor 12 for contact with a dehydrogenation catalyst, such as Pt-Sn/ZSM-5 to produce isobutene and hydrogen. The effluent stream 14 is separated in unit 16 to obtain a hydrogen rich stream 17 and an aliphatic hydrocarbon stream 18 rich in isobutene. The hydrocarbon stream 18 is combined with methanol feedstream 19 and charged to first etherification zone comprising serially connected swing reactors 20A and 20B, with inter-reactor cooling in exhnager 22. A regenerable solid metal oxide acid catalyst material, such as acid ZSM-5, is contained in swing reactors 20A, 20B, and 20C. The mixed alcoholic $C_4$ hydrocarbon feedstream contacts the solid catalyst within this reaction zone at predetermined reaction zone conditions of temperature and pressure to convert at least a portion of the feedstream to MTBE. Impurities present within the feedstock are effectively removed from the partially converted feedstream by the solid acid catalyst.

The first etherification stage comprises a plurality of fixed bed catalyst zones operatively connected for swing from one or more positions in serial production mode to rejuvenation mode in alternating sequence. Serially connected swing reactors can be employed, whereby reactor 20C, for instance, containing contaminated de-activated catalyst can be easily removed from the process and replaced immediately with a reactor containing active catalyst. Reaction zones can be serially arranged catalytic fixed bed reactors or combined into a single moving bed, slurry, or ebullated bed reaction zone. The catalytic material can be rejuvenated by contact with hydrogen-rich stream 17 at elevated temperatures.

Intermediate stream 24 containing MTBE and unreacted $C_4$ hydrocarbons and alcohol is withdrawn from reaction zone 20B and enters catalytic distillation column 30. In a preferred embodiment, the temperature of the intermediate stream is reduced prior to entering the distillation column. In distillation column 30 a substantial portion of unreacted $C_4$ hydrocarbons and alcohols are converted to MTBE over a polystyrenesulfonic acid resin catalyst such as "Amberlyst 15". Etherification over resin catalyst is carried out preferably at a temperature of about 37° to 75° C. and a pressure of about 10 to 350 psig. In a preferred embodiment acid resin catalyst is placed in an upper rectifying section 32 of a debutanizer column used for stabilizing the ethers. A product stream comprising MTBE can be withdrawn from a lower portion of distillation column 30 by line 34. Unreacted light gases are removed as by line 36.

To illustrate the common problem of catalyst poisoning when a polysulfonic acid resin catalyst is employed in the etherification process, MTBE resin catalyst unit is operated in a continuous fashion for a period of six months. Isobutene containing hydrocarbon feed is purified in a "Merox" unit and water-washed prior to entering the MTBE reactor. Conversion decreases from 93% to 52% during the six month period. Analysis identifies the contaminants on the resin catalyst. The major contaminants are nitrogen compounds, which are responsible for about 60% of the catalyst deactivation. The concentration of nitrogen on the deactivated resin catalyst is about $25 \times 10^3$ ppm. Metals such as Al, Fe, Na and Mg account for about 10% of the deactivation. The source of such metals is mainly from the water wash tower. The concentration of the metals on the deactivated catalyst is about $15 \times 10^2$ ppm. The third type of contaminant is coke. Coke is formed on the resin catalyst due to the presence of such compounds as cyclopentadiene and isoprene in the hydrocarbon feedstock. Continuous monitoring of the feedstock is necessary to control particularly the diolefinic $C_5$ hydrocarbon content. One of the advantages of the present process is that coke formation occurs primarily on the zeolite catalyst. Oxidative regeneration can be employed in addition to hydrogen stripping of zeolite catalyst to effectively remove the coke and non-volatile non-metallic contaminants from the etherification catalyst.

It is also observed that acetone and nitrile compounds are major contaminants in the hydrocarbon feedstocks which have been water washed. For example, a feed sample may contain 190 ppm acetone, 3 ppm acetonitrile and 16 ppm propionitrile. An advantage of the present process is that the hydrocarbon feedstock does not necessarily have to be water washed.

In an alternative embodiment, a multistage process is provided for etherifying $C_4^+$ aliphatic hydrocarbon feedstream containing isoalkene, wherein regenerable catalyst is employed in at least two different reaction stages. This design variation includes the steps of: a) contacting the feedstream and lower aliphatic alcohol in a first etherification reaction stage under partial etherification conditions with a regenerable inorganic metal oxide acid solid catalyst to convert a major amount of the isoalkene to $C_5^+$ tertiary-alkyl ether; b) recovering a reactant effluent from the first stage containing ether product, unreacted alcohol and unreacted olefin including isoalkene; c) charging the first etherification stage effluent to a second reaction stage catalytic distillation column containing at least a portion of regenerable inorganic metal oxide acid solid catalyst in a plurality of fixed bed catalysis- distillation zones to complete substantially full etherification of isoalkene; d) recovering $C_5+$ ether as a liquid from the catalytic distillation column; d) periodically interrupting etherification reaction in at least one reaction stage for contacting the etherification catalyst with a hot gaseous stripping stream to remove feedstock impurity and coke precursor and to substantially restore acid activity; and e) continuing ether production in the interrupted reaction stage with regenerated catalyst.

It may be advantageous to decrease operating pressure in the interrupted reaction stage during stripping, thus permitting the gaseous stripping stream to be introduced to the reaction stage at increased temperature of 450° C. or higher.

As an example of an etherification process with hydrogen rejuvenation, Zeolite Beta catalyst was used to produce TAME with FCC $C_5$ feed over a period of 40 hours. The reactions were carried at 75° C. and 400 psig with a methanol to $iC_5=$ratio of 1.2. At the end of the initial synthesis period, significant deactivation was observed, during which the iso-olefin conversion dropped from 50.1% to about 25.5%. The deactivated catalyst was then reactivated by passing a gas stream consisting essentially of $H_2$ through the reactor at pressure of 130 kPa(5 psig). In the 8 hour reactivation period, the temperature was gradually increased to 350° C. After purging with nitrogen, the reactivated catalyst was reused for producing TAME. At the same conditions as before the reactivation, the olefin conversion upon startup was 40.7%, which indicates a significant reactivation of the catalyst.

In another reactor configuration for producing TAME, the same reactivation procedure was performed. It was found that the conversion increased to 56% after reactivation, prior to which the conversion had dropped from 61.9% to 42.8%. Reactivation with $H_2$ may be further enhanced, if the temperature is increased to about 450° C. Also, greater frequency of reactivation for the catalyst will be beneficial to maintain the catalyst at high level of activity.

While the invention has been described by specific examples and embodiments, there is no intent to limit the inventive concept except as set forth in the following claims.

We claim:

1. A multistage process for etherifying a mixed $C_4+$ aliphatic hydrocarbon feedstock containing isoalkane, comprising:

contacting the hydrocarbon feedstock with dehydrogenation catalyst at elevated temperature under dehydrogenation reaction conditions to obtain $C_4+$ isoalkene and hydrogen;

separating dehydrogenation effluent to obtain an olefinic stream rich in isoalkene and a hydrogen stream;

contacting the olefinic stream and aliphatic alcohol in a first etherification stage under partial etherification conditions with a regenerable inorganic metal oxide acid solid catalyst to convert a major amount of the isoalkene to $C_5+$ tertiary-alkyl ether;

recovering a reactant effluent from the first stage containing ether product, unreacted alcohol and unreacted olefin including isoalkene;

charging the first etherification stage effluent to a second stage catalytic distillation column containing solid acid resin etherification catalyst in a plurality of fixed bed catalysis-distillation zones to complete substantially full etherification of isoalkene;

recovering $C_5+$ ether as a liquid from the catalytic distillation column;

contacting the first stage etherification catalyst with said hydrogen stream to remove feedstock impurity and coke and to restore acid activity: and continuing ether production with regenerated catalyst.

2. The process of claim 1 wherein the alcohol consists essentially of methanol, the first stage catalyst comprises medium pore zeolite, and the second stage catalyst comprises polymeric sulfonic acid resin.

3. The process of claim 1 wherein the $C4+$ feedstock comprises predominantly of $C_4$ hydrocarbons containing isobutane.

4. The process of claim 1 wherein the first etherification stage comprises a plurality of fixed bed catalyst zones operatively connected for swing from production mode to regeneration mode in alternating sequence.

5. The process of claim 1 wherein the first etherification stage comprises a fluidized bed reaction zone for maintaining a solid particulate acid catalyst, and further including the steps of withdrawing a portion of the solid particulate catalyst from etherification production for regeneration; regenerating the solid particulate catalyst at elevated temperature to remove inactivating impurities and coke and to restore acid activity; and returning regenerated catalyst to ether production.

6. The process of claim 1 wherein the mixed olefin feedstock contains impurity selected from nitrogen compounds; Al, Fe, Na and/or Mg metal; butadiene, isoprene or cyclopentadiene.

7. The process of claim 1 wherein the first etherification reaction stage concurrently removes feedstock impurities by deposition of said impurities on said metal oxide catalyst.

8. The process of claim 1 wherein the first etherification stage comprises at least two serial reactor zones wherein a first reactor zone is maintained at least 5° C. higher than a second reactor zone.

9. The process of claim 1 wherein the second stage catalytic distillation column reaction zone operates at a temperature about 10°-30° C. lower than the first stage.

10. The process of claim 1 wherein the aliphatic alcohol comprises methanol, ethanol or isopropanol.

11. A continuous multistage process for preparing methyl tert-butyl ether comprising:

maintaining two reaction zones in series arrangement, a first reaction zone containing solid crystalline acid medium pore metallosilicate catalyst particles and a second reaction zone containing acid resin catalyst;

contacting a mixed feedstock comprising methanol and isobutene-containing $C_4$ hydrocarbons with the solid metallosilicate catalyst particles in the first reaction zone under etherification conditions to obtain an intermediate product comprising methyl t-butyl ether and unreacted feedstock;

withdrawing an intermediate product stream from first reaction zone;

contacting at least a portion of the intermediate product stream with acid resin catalyst in the second zone under etherification conditions to obtain a product comprising a major amount of methyl t-butyl ether.

removing first reaction zone from on-line contact with feedstock;

regenerating the solid catalyst particles in the first reaction zone by stripping with a non-oxidative gaseous stream; and resuming addition of feedstock to the first reaction zone.

12. A process according to claim 11 further comprising the steps of withdrawing the product comprising a major amount of ether from the second reaction zone; subjecting the product to fractionation to obtain a purified ether; and recovering purified ether.

13. A process according to claim 11 wherein the solid acid catalyst particles comprise aluminosilicate zeolite having the structure of ZSM-5, ZSM-11, ZSM-12, ZSM-35, ZSM-50, MCM-22 or zeolite Beta.

14. A process according to claim 11 wherein the acid resin catalyst comprises a macroreticular polystyrene-sulfonic acid catalyst.

15. A multistage process for etherifying $C_4+$ aliphatic hydrocarbon feedstream containing isoalkene, comprising:

contacting the feedstream and lower aliphatic alcohol in a first etherification reaction stage under partial etherification conditions with a regenerable inorganic metal oxide acid solid catalyst to convert a major amount of the isoalkene to $C_5+$ tertiary-alkyl ether;

recovering a reactant effluent from the first stage containing ether product, unreacted alcohol and unreacted olefin including isoalkene;

charging the first etherification stage effluent to a second reaction stage catalytic distillation column containing at least a portion of regenerable inorganic metal oxide acid solid catalyst in a plurality of fixed bed catalysis- distillation zones to complete substantially full etherification of isoalkene;

recovering $C_5+$ ether as a liquid from the catalytic distillation column;

periodically interrupting etherification reaction in at least one reaction stage for contacting the etherification catalyst with a hot gaseous stripping stream containing hydrogen to remove feedstock impurity and coke precursor and regenerate said catalyst; and continuing ether production in the interrupted reaction stage with said regenerated catalyst.

16. The process of claim 15 wherein operating pressure is decreased in the interrupted reaction stage during stripping; and wherein the gaseous stripping stream contains hot hydrogen introduced to the reaction stage at temperature of at least 450° C.

* * * * *